United States Patent
Catani et al.

(10) Patent No.: US 6,984,732 B2
(45) Date of Patent: Jan. 10, 2006

(54) HIGH-INTENSITY SWEETENER COMPOSITION AND DELIVERY OF SAME

(75) Inventors: Steven Catani, Athens, GA (US); Anne-Lise Lucas, Princeton, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 10/403,918

(22) Filed: Mar. 31, 2003

(65) Prior Publication Data

US 2004/0191400 A1    Sep. 30, 2004

(51) Int. Cl.
*C13K 13/00*    (2006.01)
*C07H 3/04*    (2006.01)

(52) U.S. Cl. .................. 536/123.13; 536/4.1; 536/122; 536/1.1; 536/123.1; 426/548; 426/658

(58) Field of Classification Search ........... 536/123.13, 536/4.1, 122, 1.1, 123.1; 426/548, 658
See application file for complete search history.

(56) References Cited

U.S. PATENT DOCUMENTS

| | | | |
|---|---|---|---|
| 3,869,555 A | | 3/1975 | Heonis |
| 3,892,867 A | | 7/1975 | Schoonman |
| 4,061,783 A | | 12/1977 | Hoffman et al. |
| 4,806,261 A | | 2/1989 | Ciallella et al. |
| 4,925,683 A | | 5/1990 | Fischbach et al. |
| 4,973,416 A | | 11/1990 | Kennedy |
| 5,125,534 A | | 6/1992 | Rose et al. |
| 5,204,115 A | * | 4/1993 | Olinger et al. ............... 424/470 |
| 5,300,305 A | | 4/1994 | Stapler et al. |
| 5,380,541 A | * | 1/1995 | Beyts et al. ................. 426/548 |
| 5,440,976 A | | 8/1995 | Giuliano et al. |
| 5,498,709 A | | 3/1996 | Navia et al. |
| 5,620,707 A | | 4/1997 | Sanker et al. |
| 6,238,690 B1 | | 5/2001 | Kiefer et al. |
| 2002/0012689 A1 | | 1/2002 | Stillman |
| 2002/0120134 A1 | | 8/2002 | El Kabbani et al. |
| 2002/0122823 A1 | | 9/2002 | Bunick |

FOREIGN PATENT DOCUMENTS

| | | |
|---|---|---|
| CA | 2253386 A | 4/1997 |
| EP | 1 442 282 | 9/1964 |
| EP | 0708110 A2 | 4/1996 |
| WO | WO 92/10168 A1 | 6/1992 |
| WO | WO 97/41835 A | 11/1997 |
| WO | WO 00/57725 A1 | 10/2000 |
| WO | WO 01/70591 A1 | 9/2001 |

OTHER PUBLICATIONS http://www.nysaes.cornell.edu/fst/fvc/Venture/venture2_chemical.html (Venture, Summer 1998 vol. No. 2).*
http://www.speclab.com/compound/c65850.htm (Spectrum: chemical Fact Sheet).*

* cited by examiner

*Primary Examiner*—Samuel Barts
*Assistant Examiner*—Michael C. Henry

(57) ABSTRACT

A composition for sweetening ingestable solids or liquids. The composition is compressed and comprises less than about 7.5 weight-% sucralose and one or more diluents. The composition is compressed at a pressure of greater than 2 pounds per square inch. A method of forming the composition and a system for delivering the composition are also provided.

13 Claims, 3 Drawing Sheets

HIGH-INTENSITY SWEETENER COMPOSITION AND DELIVERY OF SAME

TECHNICAL FIELD

The present invention is directed to a composition for a compressed high intensity sweetener that maintains color stability, to a method of forming the composition, and to a system for delivering the composition.

BACKGROUND OF THE INVENTION

Consumers have a wide variety of individual tastes, particularly with regard to their preferred level of sweetness in foods and beverages. Limitations relating to production abilities, shipping quantities, and shelf space, however, restrict the ability of a manufacturer as to the variety of foods and beverages that can be offered to the consumer. Furthermore, in some instances, the consumer desires to sweeten a consumable item to a unique, personalized level rather than be limited to the choices provided by the food or beverage manufacturer. A large market has arisen, therefore, seeking to provide packaged sweeteners to consumers. Such sweeteners allow the consumer to sweeten foods and beverages to their individual tastes.

Sucralose (4,1',6'-trichloro-4,1',6'-trideoxy-galactosucrose) is a high-intensity sweetener made from sucrose that can be used in many food and beverage applications. Sucralose is generally made following procedures set forth in U.S. Pat. Nos. 4,362,869; 4,380,476; 4,801,700; 4,950,746; 5,470,969; and 5,498,709, as well as in pending U.S. patent application Ser. No. 09/991,123, the disclosures of each of which are incorporated in this document by reference. Sucralose may be provided for consumer use in a number of forms useful in the sweetening of foods and liquids. These forms include sachets, tubular packets, liquid drops, tablets, and granules or crystals.

In all of these forms, the intensity of the sweetener requires that the high-intensity sweetener be diluted with a non-sweet or less-sweet compound to make use practical. For example, a teaspoon of sucrose weighs about 4 grams. The equivalent amount of sucralose would be 0.007 grams. This amount of material would be very hard to put into a sachet consistently, and would be nearly impossible to transfer from the sachet to a liquid, such as coffee, which a user desires to sweeten. As a result, a typical sachet contains sucralose diluted 20–100 times with a carrier such as dextrose. All consumer forms—including tablets, granules, and liquid drops—are diluted to facilitate delivery.

All of the conventional forms have some limitation. First, the use of the diluent adds weight and volume to the product, while adding no appreciable value, and increases the processing and shipping costs. Second, the diluent reduces the applicability of the product; diluents are often unacceptable to certain members of the population. For example, food-grade carbohydrate carriers, such as dextrose and maltodextrin, are not acceptable to people on restricted carbohydrate diets. Fiber-based carriers are unacceptable to people subject to gastrointestinal (GI) distress. Liquid products require single-use packaging or preservatives to prevent microbial contamination, making them unacceptable to people who avoid the use of common preservatives.

Therefore, dry (rather than liquid) forms of sucralose, such as tablets, granules, and sachets, are often desired for sweetening liquids. Tablets are a popular consumer form for delivery of most high-intensity sweeteners. They are particularly well suited for use in sweetening beverages, such as coffee. In fact, in some markets, particularly the United Kingdom and Australia, tablets command the highest market share of all the consumer forms. Tablets are currently available containing all of the commercial sweeteners including aspartame, acesulfame, saccharine, sucralose, as well as some of the protein-based sweeteners such as stevia. Commercially available tablets are produced using conventional tableting equipment and formulation technology.

The art of delivery systems is replete with various types of systems used to deliver solid food, liquids, drugs, and other necessary items. The Hayshiabara Company of Japan has long sold a drug delivery system, for example, in which the drug is impregnated into a dissolvable, ingestable polymer strip. The dissolvable strip technology has recently become popular as a way to deliver other intense ingredients such as breath fresheners. This form could be used to deliver a high-intensity sweetener but is limited in its ability to carry large amounts of sweetener and would apply only to very intense sweeteners such as sucralose or neotame. Other sweeteners would require very large strips to carry a reasonable amount of sweetener. Large strips would work, but would create issues associated with the GI impact of the large polymer dose.

U.S. Pat. No. 5,620,707 issued to Sanker et al. is directed to seamless beadlets for customization of flavor and sweetener in a beverage. The beadlet comprises a shell material with a core composition in the material of the shell material suitable for ingestion. Examples of these materials are gelatin, polyvinyl alcohols, waxes, and gums. The shell material forms a pocket in which the core of the material is contained. The core material that is used for flavoring the beverage contains a flavor component as well as a sweetener component comprising acetosulfame and a second sweetener selected from a specified class of compounds. The shell material may be formed in a variety of shapes, such as spheres, oblong shapes, disks, puffed squares, and cylinders.

Similarly, U.S. Pat. No. 6,238,690 is directed to food products containing seamless capsules and methods of making the same. The patent describes consumable products that are made of a seamless capsule with an outer shell. The outer shell is made of a carbohydrate material and encloses an inner core that may include beverages, as well as other foodstuffs.

U.S. Pat. No. 5,300,305 is directed to breath protection microcapsules. The shell materials that are used in the microcapsules are suitable for ingestion and may be formed in a variety of shapes. Various materials may be enclosed within the shell material and these include sweeteners such as sugar, saccharine, and aspartame.

U.S. Pat. No. 4,925,683 is directed to beverage capsules and describes a beverage base that is enclosed in a thin-walled solid envelope made of chocolate or a fat-based confectionery coating. This patent cites French Patent No. 1,442,282, which describes a food product comprising beverage powders surrounded by an envelope of sugar, enabling two different products to be taken in a single operation and their instantaneous dissolution together.

U.S. Published Patent Application No. 2002/0012689 describes liquid-activated infusion packet systems whereby the enveloping materials may be totally or partially edible. The packets may enclose materials including various flavors, as well as pharmaceutical and dietary supplements. Also described are a number of packet systems that are used for a variety of purposes including the delivery of sweetening agents.

Sucralose is very stable as long as it contains at least 0.5 weight-% moisture (as disclosed by El Kabani et al. in U.S.

patent application Ser. No. 09/991,123). When less mositure is present, sucralose can break down, resulting in browning or brown spotting (i.e., discoloration) of the dry material. Although the problem exists at room temperature, at higher temperatures of about 40° C. to 55° C., which can occur in transport and storage (e.g., warehouse) environments, tablet forms of sucralose, even with higher levels of moisture present, can form spots in as little as three days. The problem is exacerbated when increased pressure is applied, such as during compression of the sucralose to form tablets and other compressed forms.

Thus, despite the very high stability of sucralose in food and beverage applications, when powdered crystalline sucralose is compressed into a tablet form an instability is often created that manifests itself as brown spotting or browning (i.e., discoloration). Although such tablets show no discernable loss of sweetness and the breakdown products have been thoroughly tested for safety as part of the federal Food and Drug Administration food additive petition process, the discoloration renders the product unacceptable to most consumers. To maintain consumer acceptance, therefore, sucralose must be color stable (i.e., remain white).

Interestingly, the inventors named on U.S. patent application Ser. No. 09/991,123, El Kabani et al., disclose that a moisture content of between 0.5 and 10 percent by weight in loose powdered sucralose can greatly enhance its stability. They also disclose that addition of a buffer to the sucralose solution before crystallization significantly increases the stability of the sucralose crystallized from the solution. The inventors still further disclose that, by maintaining the pH of the sucralose-containing crystallization solution in the range of 5.5 to 8.5 during the crystallization process, the stability of the final crystalline sucralose can be improved. Further, sachets containing sucralose and a variety of incipients having between 0.5 weight-% and 10 weight-% moisture behave in a stable manner. Despite the presence of moisture, however, tablets containing compressed forms of sucralose experience bowning and brown spotting. Accordingly, there remains a need for an improved sucralose composition that resists discoloration.

To overcome the shortcomings of existing dry sucralose compositions, the method of forming such compositions, and the systems used to deliver such compositions, a new sucralose composition is provided. Also provided is a method of forming and a system for delivering the composition. An object of the present invention is to provide an improved sucralose composition. Related objects are to provide an improved method of forming the composition and an improved system for delivering the composition. Another object is to provide an improved sucralose composition that exhibits increased stability. It is still another object of the present invention to reduce the risk of discoloration in a sucralose composition.

SUMMARY OF THE INVENTION

To achieve these and other objects, and in view of its purposes, the present invention provides a composition for sweetening ingestable solids or liquids, a method of forming the composition, and a system for delivering the composition. The composition essentially consists of:

less than about 7.5 weight-% sucralose; and one or more diluents;

the composition being compressed at a pressure of greater than 2 pounds per square inch.

In a further aspect, the present invention provides a method for forming a compressed sucralose composition, the method consisting of the steps of:

crystallizing sucralose;

combining less than 7.5 weight-% crystallized sucralose with one or more diluents to form a sweetener composition; and compressing the sweetener composition at a pressure of greater than 2 pounds per square inch. In a still further aspect, the present invention provides various systems for delivery of a sucralose composition with high color stability.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

Figure 1:
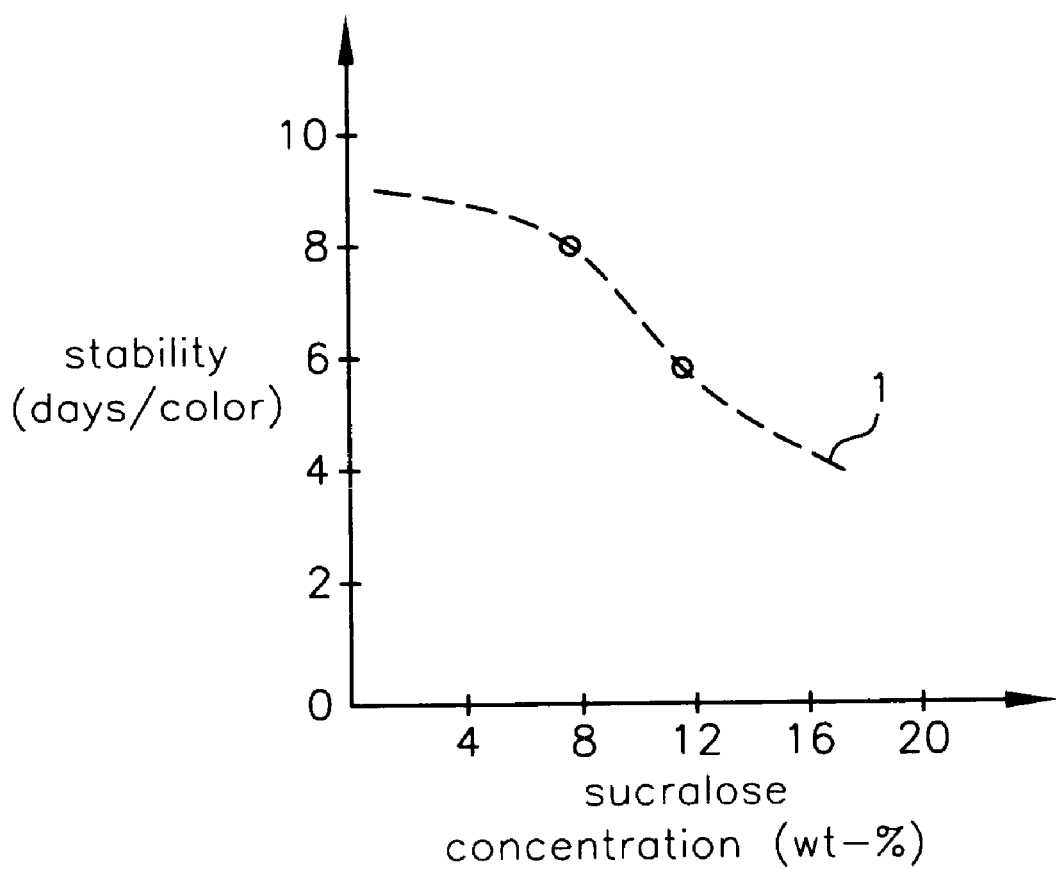
FIG. 1 is a graph showing color stability for an exemplary compressed sucralose composition according to the present invention versus sucralose concentration.

As used herein the term that "Loose sucralose" is intended to mean that sucralose is compressed by its own weight at less than about 1 pound per square inch (psi). Although the color of loose sucralose can be controlled by maintaining the moisture content at from 0.5 to 10 percent by weight, as disclosed by El Kabani et al. in U.S. patent application Ser. No. 09/991,123, the present inventors have determined that the color stability for compressed sucralose compositions (i.e., compressed at a pressure of greater than 2 psi) can vary to unacceptable levels even at this range of moisture content. The inventors have further determined that, for compressed sucralose compositions, color stability can be maintained at an acceptable level by carefully controlling the sucralose concentration in a sucralose composition.

The inventors have found that by adding a diluent to the sucralose composition to be compressed (e.g., in tablet form), above a critical level, the discoloration or spotting problem can be avoided. The level is critical but a wide range of diluents have been shown to be feasible. Suitable diluents include sweet or non-sweet natural and modified carbohydrate, sugar alcohols, food acids, sodium carbonate, and food acid salts. Interestingly, the list also includes diluents like citric and ascorbic acid. Acids are typically reported to accelerate the breakdown of carbohydrates.

At sucralose concentrations of about 11.5 weight-%, spotting occurs at high temperatures in a short period. When more dilute tablets are formed (i.e., less than 7.5 weight-% sucralose), even with food acid diluents and even at low moisture levels, more stable tablets can be made. Although not essential to the present invention, it will be clear that the diluent can also serve to add a flavor to the application, or a health benefit (such as a fiber) to the tablet, enhancing its use while preventing spotting.

The use of non-moisture diluents to enhance sucralose stability will be surprising to those skilled in the art. El Kabani et al. disclose that moisture and bases or buffers can make neat (i.e., 100%) sucralose more stable by scavenging chlorine released in early stages of degradation, thereby preventing self-promoting break down of the sucralose. Excipients, such as carbohydrates or food acids, would not scavenge chlorine and therefore, would not be expected to prevent break down of sucralose.

Color Stability

"Color stability" is the ability of a composition to maintain a desired coloration over time in an environment having a temperature of 55° C. and 100% relative humidity. Color stability is measured in color-days (days divided by color value), a rating value obtained by exposing a sample to an environment of about 55° C. and a relative humidity of 100%. The color of the sample is observed for colorization on an incremental scale ranging from white (having a value of 1) to dark brown (having a value of 10). The color-days rating for a composition is derived by dividing the number of days of exposure of the composition by the average color value for the composition following that exposure.

For example, a sucralose compound is exposed to the test environment of 55° C. and 100% relative humidity for 10 days. Following the 10-day exposure, the average color of the sucralose compound is 2. This compound has a color-days rating of 5 (10 days divided by an average color value of 2).

As illustrated in FIG. 1, the graphed curve labeled 1 shows that the stability of a compressed sucralose composition, measured as color-days, improves dramatically and unexpectedly at a sucralose concentration of less than 11.5 percent by weight. These results are unexpected because (a) the differences in the concentration are relatively small, and (b) autocatalytic compositions do not generally have wide variations in stability over small changes in concentration.

Compressed Sucralose

As discussed above, El Kabani et al. (U.S. patent application Ser. No. 09/991,123) disclose a method for maintaining stability of sucralose by controlling the moisture content at between 0.5 and 10 percent by weight. The data presented by El Kabani et al. are for loose sucralose. Loose sucralose compositions typically are compressed only by the weight of the sucralose itself, resulting in compression of less than 1 psi. In certain delivery forms, such as tablets, a sucralose composition is in a compressed form. The compressed forms of sucralose are compressed by pressure applied to the sucralose composition during fabrication. The inventors have determined that controlling the moisture content does not maintain stability of a compressed sucralose composition. This lack of stability is demonstrated by test data presented in Table C and described below.

Tablets

Figure 3:
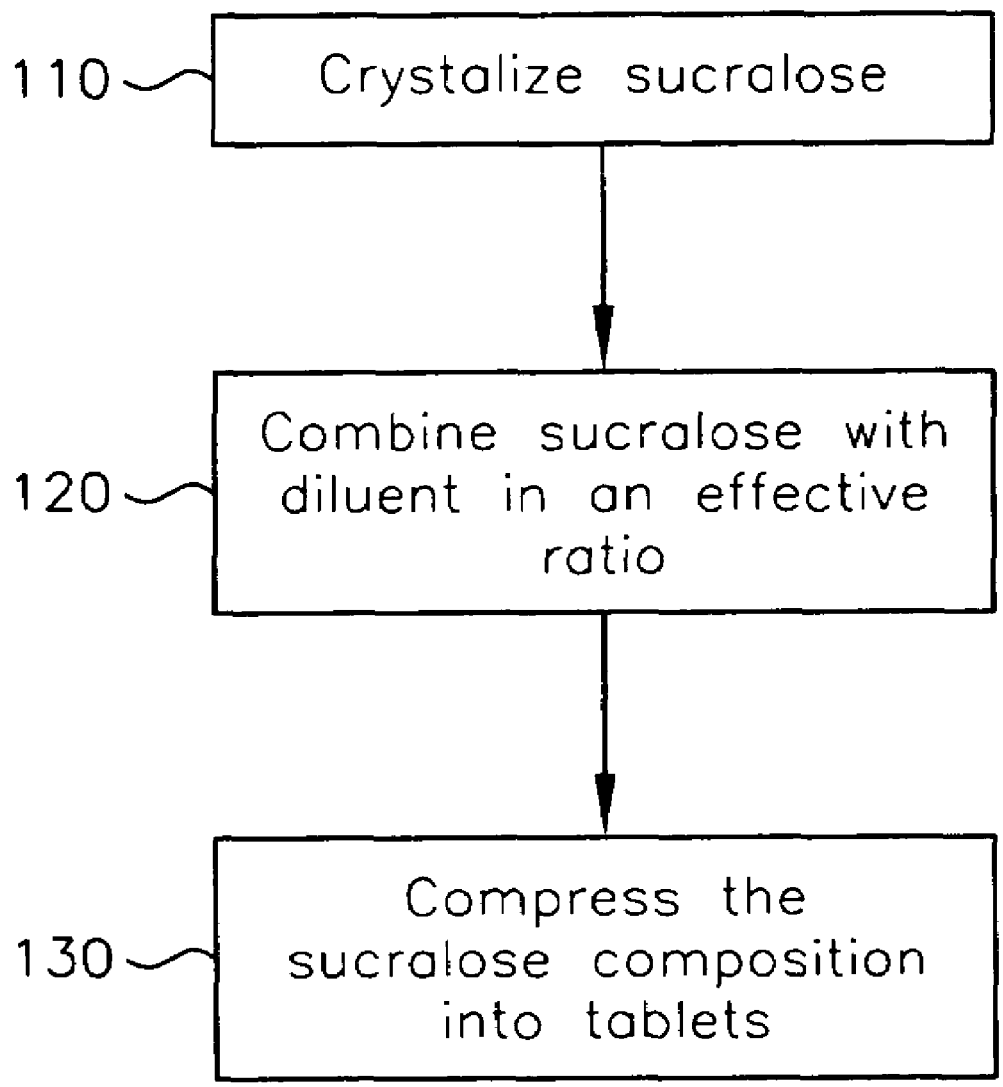
FIG. 3 is a flow diagram of an exemplary method for fabricating a low-sucralose tablet according to the present invention.

One form of compressed sucralose is a tablet. Following is a description of a composition and method for forming an exemplary sucralose tablet. As shown in FIG. 3, the sucralose is crystallized (STEP 110). An exemplary method for crystallizing sucralose is provided in U.S. patent application Ser. No. 09/991,123. The crystallized sucralose is then combined with one or more diluents (STEP 120) in an effective ratio to form a sucralose or sweetener composition. The diluent or diluents may include bulk fillers, such as carbohydrates, low intensity sweeteners, or the like. Proteins, starches, amino acids, and disintegration agents may also be used as diluents to provide desirable tablet properties, as is known in the art. An effective ratio of sucralose to diluent is a ratio that produces improved stability in a compressed sucralose composition, consistent with the test results for a low sucralose composition presented in Table C. According to the present invention, an effective ratio is less than about 7.5 percent sucralose by weight. The composition may be dry (i.e., contain no moisture and maintain its stability). Alternatively, the composition may further include moisture at a concentration of less than about 10 weight-%.

The sucralose composition is compressed in a tablet press (STEP 130) to form tablets. In an exemplary fabrication method, tableting is accomplished in a FETTE 3090 rotary tablet press (available from Fette AMERICA of Rockaway, N.J.). The tablet height is controlled by combined control of feed and pressure. The nominal pressure used is 20 kilo-newtons. The press is automatically adjusted within preset limits to ensure that the tablet height is kept within the specified tolerances. The size and shape of the tablet are determined by the shape of the die selected to compress the sucralose composition.

The tablet ingredients for a low sucralose composition according to an exemplary embodiment of the present invention are listed in Table A. The diluents listed in Table A (i.e., the ingredients other than sucralose) are exemplary, and do not limit the invention. Tablet ingredients are also listed in Table A for a high sucralose composition, which the inventors have determined provides an unacceptable color stability. As will be described below, the low sucralose composition provides superior color stability as compared to the high sucralose composition.

TABLE A

|  | High Sucralose | Low Sucralose |
|---|---|---|
| Tablet Size (mg): | 55 | 55 |
| Direct Compression Lactose: (wt-%) (Tablettose ® in UK) | 56.2 | 57.0 |
| Lactose Monohydrate: (wt-%) | 20 | 22.41 |
| Sucralose: (micronised) (wt-%) | 11.6 | 7.76 |
| Cross-Linked Carboxymethylcellulose: (CMC) (wt-%): | 2.0 | 2.0 |
| L-Leucine (wt-%): | 10 | 10.63 |
| Magnesium Stearate: (wt-%) | 0.2 | 0.2 |
| Total: | 100% | 100% |

The sucralose tablets described above are compressed at 20 kilo-newtons over a 6 mm tablet, or at a pressure of about 8,000 psi. The composition may be compressed at a pressure greater than about 5,000 pounds per square inch and more preferably at a pressure greater than about 7,000 pounds per square inch. By contrast, loose packed sucralose with a bulk density of 30 pounds per cubic foot packed in a supersack which is 4 feet high has a compressive pressure at its highest point of about 0.85 psi.

Delivery System

Figure 2:
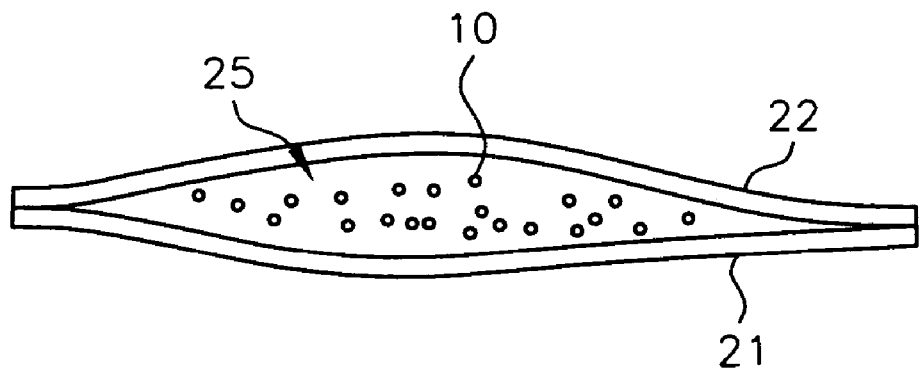
FIG. 2 is a sectional view of an exemplary delivery device for compressed sucralose according to the present invention.

In an exemplary embodiment of an alternative form of compressed sucralose, as shown in FIG. 2, a sucralose composition 10 is delivered in the interstitial space between two sheets of film 21, 22. This delivery system has a ravioli-like form. The delivery amount of sucralose is not impregnated in the film 21, 22 but is carried in a pocket 25; the size of pocket 25 is variable. The advantages of this delivery form will be clear to those skilled in the art, from the following description. For example, a film pocket may be used to reduce the size of the delivery system for a teaspoon of sugar equivalent by a factor of 10 and the amount of polymer by 20% or more as compared to an encapsulation.

The film 21, 22 is preferably an edible, water-soluble material and, more preferably, solely a carbohydrate-based material. Film 21, 22 may include an oligosaccharide, preferably a water-soluble polysaccharide, such as pullulan (manufactured by Hayashibara Biochemical Laboratories in Okayama, Japan). The dissolvable film 21, 22 is easily manufactured and sealed at its edges to form pocket 25. Film 21, 22 may be two separate layers of film or a single film folded back upon itself. Thus, the pocket 25 may be created by sealing the edges of two strips or by folding a strip and then sealing the remaining edges. Film 21, 22 is stable in typical storage and transport environments and dissolves easily in liquids to release the sucralose composition 10.

Although the ravioli form works with a neat high intensity sweetener (e.g., 100% sucralose), the form can also deliver a composition comprising a sweetener and various flavors. This feature allows the system to be an ideal delivery vehicle for nutritional ingredients and a convenient way to make single-serve beverages. The ravioli delivery system may also eliminate the need to amalgamate or size-modify the constituents to facilitate consistent delivery. Ingredients can be added to enhance dissolving and mixing of the sweetener and flavors. For example, a dry carbonate form and acid could be included that produce $CO_2$ on wetting.

Several shapes can be used for the films 21, 22, including round, square, and rectangular ravioli-like forms, and films with carved or cast out pockets. Custom shapes may be used to cue the user to their contents. It is also possible for the delivery system to have multiple pockets allowing ingredients, which are not compatible, to be held separately until they are used.

Figure 4:
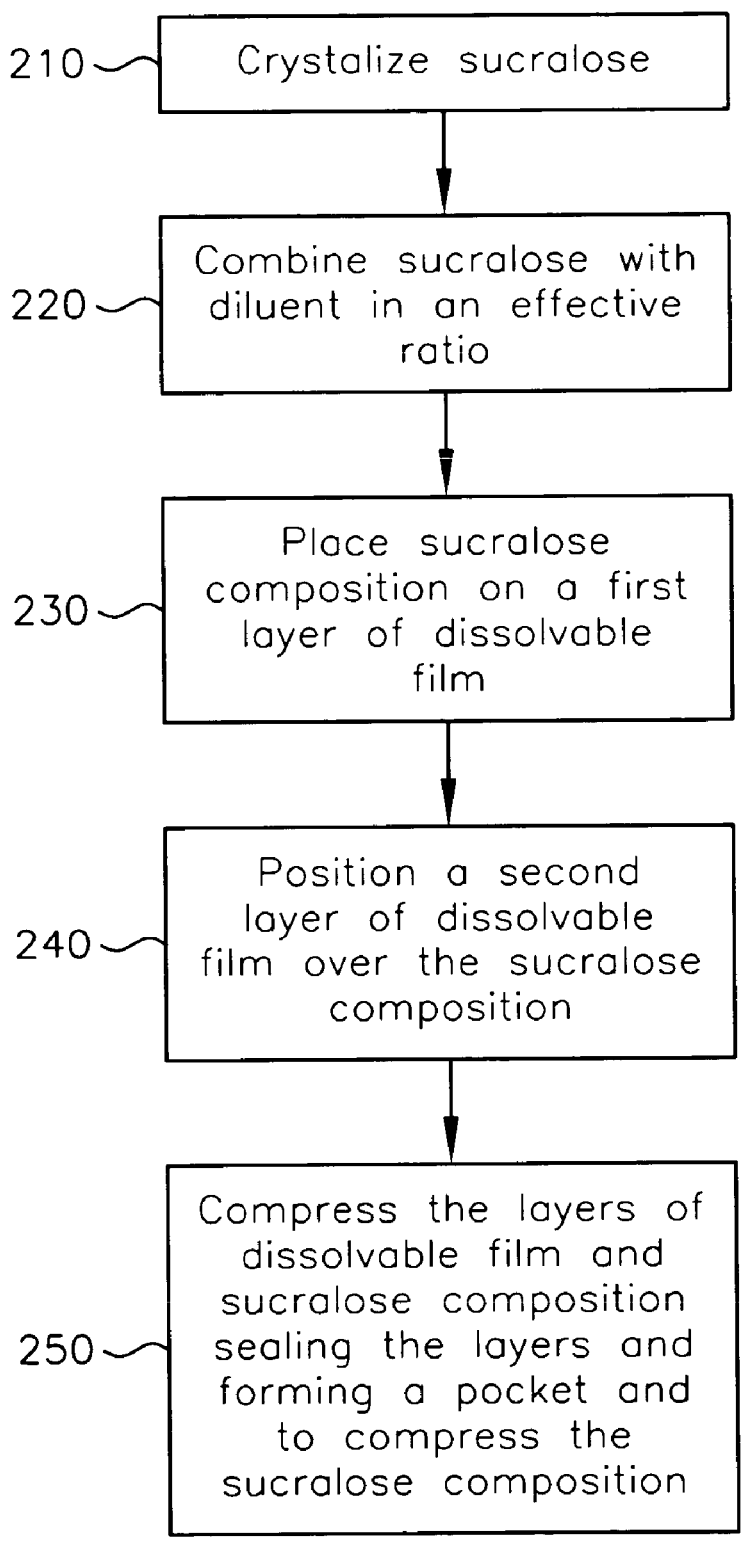
FIG. 4 is a flow diagram of an exemplary method for fabricating a low-sucralose delivery system according to the present invention.

As shown in FIG. 4, an exemplary method for forming a ravioli-type delivery system is provided. First, sucralose is crystallized (STEP 210). The crystallized sucralose is then combined with one or more diluents (STEP 220) in an effective ratio to form a sucralose or sweetener composition. As with the tablets described above, the diluent or diluents may include bulk fillers, such as enzymes, low-intensity sweeteners, or the like. Proteins, starches, carbohydrates, and disintegration agents may also be used as diluents.

The sucralose composition 10 is placed on a first layer of dissolvable film 21 (STEP 230). This step may be accomplished, for example, by advancing the first layer of dissolvable film 21 on a conveyor and depositing a metered quantity of the sucralose composition 10 on the first layer of dissolvable film 21 at functional intervals.

A second layer of dissolvable film 22 is positioned over the sucralose composition 10 (STEP 240). Then the first and second layer of dissolvable film 21, 22 and the sucralose composition 10 are compressed (STEP 250), for example, by a die, a roller, or the like. The compressed layers of dissolvable film 21, 22 are sealed at their edges, and the sucralose composition 10 is compressed at a pressure of greater than about 2 psi.

Although the invention has been described above in terms of either compressed tablets or a ravioli-like form, other closely packed forms can also be used as long as the composition has the correct diluent level.

Testing

Tablets were prepared using the tableting process described above and the high-sucralose and low-sucralose compositions in Table A. The distribution of diluents was consistent for the tablets as shown in Table B.

TABLE B

| Distribution of Diluents | | |
|---|---|---|
| Diluent | High-Sucralose | Low-Sucralose |
| Lactose (wt-%): | 86.2 | 86.1 |
| CMC (wt-%): | 2.3 | 2.2 |
| l-Leucine (wt-%): | 11.3 | 11.5 |
| Magnesium Stearate (wt-%): | 0.2 | 0.2 |

Table B shows that the only significant change from high to low sucralose test tablets was the sucralose concentration. Accordingly, the difference in color stability, as shown in Table C and described below, is caused by the difference in sucralose concentration; compare the high-sucralose composition and the low-sucralose composition.

The high-sucralose and low-sucralose test tablets were placed in an open dish and subjected to accelerated stability testing in an environment heated to 55° C. and 100% relative humidity, then inspected for color development. Color was assessed visually and rated on a relative scale of 1 (white) to 10 (dark brown). Stability ratings were then calculated as the quotient of the number of days subjected to test conditions divided by the average color rating at a given time. Larger values reflect greater stability. The test results are presented in Table C.

TABLE C

| Test Results | |
|---|---|
| % Sucralose | Days/Color |
| 7.76 | 8.0 |
| 11.6 | 5.9 |

The low-sucralose tablets (7.76 wt-% sucralose) are shown to have a significantly better stability (larger value for color stability or Days/Color) than the high-sucralose tablets (11.6 wt-% sucralose).

The illustrated composition includes a bulk ingredient (lactose), a disintigration agent (CMC), an amino acid (L-Leucine), and a lubricant (magnesium stearate). Other diluents may be incorporated to provide advantageous qualities to the composition. For example, sugar alcohols, food acids, food acid salts, or a combination of these materials may be added to the composition or substituted into the composition to provide flavoring to the food or liquid being sweetened. Carbohydrates may be used as the bulk ingredient as in the illustrated example. Other bulk ingredients, such as sucrose may used as a bulk ingredient in addition to or in place of carbohydrates. Alternatively, one or more of the diluents may be omitted or the amounts may be adjusted, provided that the sucralose composition is controlled at less than 7.5 weight-%. Alternatively, the sucralose concentration may be controlled at less than 5 weight-% to provide enhanced stablility.

Although illustrated and described above with reference to certain specific embodiments and examples, the present invention is nevertheless not intended to be limited to the details shown. Rather, various modifications may be made in the details within the scope and range of equivalents of the claims and without departing from the spirit of the invention. The examples are included to more clearly demonstrate the overall nature of the invention; they are exemplary, not restrictive, of the invention. More specifically, the sweetener may be sucralose, as highlighted in the discussion above, but the principles of the present invention might also apply to other high-intensity sweeteners. The sweetener may be combined with flavors, a dispersing agent, or both.

What is claimed is:

1. A composition for sweetening ingestible solids or liquids, the composition comprising moisture at a concentration of less than 10 weight-% and being a compressed form prepared by a method including the step of applying a pressure of greater than two pounds per square inch to a mixture, the mixture comprising:
   from about 7.5 to about 5 weight-% of sucralose; and
   one or more diluents, wherein said one or more diluents comprises at least one of a disintegration agent, a food acid, or a food acid salt.

2. The composition of claim 1 wherein the one or more diluents comprise a carbohydrate.

3. The composition of claim 1 wherein the one or more diluents comprise a sugar alcohol.

4. The composition of claim 1 wherein the one or more diluents comprise a food acid.

5. The composition of claim 1 wherein the one or more diluents comprise a sodium carbonate.

6. The composition of claim 1 wherein the one or more diluents comprise a food acid salt.

7. The composition of claim 1 wherein the composition has a color-days rating of greater than 8.

8. The composition of claim 1 wherein the composition maintains a white color for at least 8 days.

9. The composition of claim 1 wherein the composition is compressed at a pressure of greater than 5,000 pounds per square inch.

10. The composition of claim 1 wherein the composition is formed into a tablet.

11. The composition of claim 1 wherein the composition is retained in the interstitial space between two sheets of dissolvable film.

12. The composition of claim 1 wherein the one or more of the diluents comprise one or both of flavors and dispersing agents.

13. A tablet for sweetening an ingestible solid or liquid, the tablet comprising moisture at a concentration of less than 10 weight-% and being a compressed form prepared by a method including the step of applying a pressure of greater than 7,000 pounds per square inch to a mixture, the mixture comprising:
    from 7.5 to 5 wt-% crystallized sucralose; and
    one or more diluents; wherein said one or more diluents comprises least one of a disintegration agent, a food acid, or a food acid salt.

* * * * *